United States Patent [19]

Schainholz

[11] 4,135,868
[45] Jan. 23, 1979

[54] SUPPORTS FOR INSTRUMENT STERILIZATION

[76] Inventor: Herbert Schainholz, 316 Locust St., Teaneck, N.J. 07666

[21] Appl. No.: 784,717

[22] Filed: Apr. 5, 1977

[51] Int. Cl.² .................. A61B 19/02; A61L 3/00; A61L 3/02
[52] U.S. Cl. .................. 422/310; 422/300; 312/209; 211/60 R; 211/60 T; 206/438
[58] Field of Search .................. 21/105, 82 R–90; 211/60 R, 60 T, 184; 248/201; 206/372, 373, 379, 306, 438; 312/111, 209

[56] References Cited

U.S. PATENT DOCUMENTS

| 402,550 | 4/1889 | Willbrandt | 21/82 H |
|---|---|---|---|
| 1,939,497 | 12/1933 | Herring | 205/373 |
| 2,551,859 | 5/1951 | Thompson | 21/88 |
| 2,645,334 | 7/1953 | Aldridge | 206/306 |
| 2,833,007 | 5/1958 | Messer et al. | 21/82 R |
| 2,984,344 | 5/1961 | Weissman | 21/84 |
| 3,154,281 | 10/1964 | Frank | 248/201 |
| 3,723,061 | 3/1973 | Stahl | 21/83 |
| 3,954,184 | 5/1976 | Mendenhall | 211/184 |
| 4,043,754 | 8/1977 | Sklar | 21/105 |

*Primary Examiner*—Morris O. Wolk
*Assistant Examiner*—Bradley Garris

[57] ABSTRACT

Modular supports for instruments in a sterilization tray having a bottom and a cover each containing an array of apertures, and each support comprising an integrally molded rectangular instrument support base with downward projecting longitudinally split buttons to be inserted in the tray bottom apertures. Each instrument support base has upstanding members with a slot therebetween to receive and hold selected strips notched on their upper edges to cradle and support instruments for sterilization.

A hold-down base has upwardly extending buttons to be inserted in the tray cover apertures including a wide slot to hold a downwardly extending block of resilient material for contacting instruments cradled in the strip notches. A bracket with a longitudinal fin inserted in the slot of an instrument support base fixed to the cover may also hold a resilient block to be used as a hold-down.

5 Claims, 12 Drawing Figures

U.S. Patent   Jan. 23, 1979   4,135,868
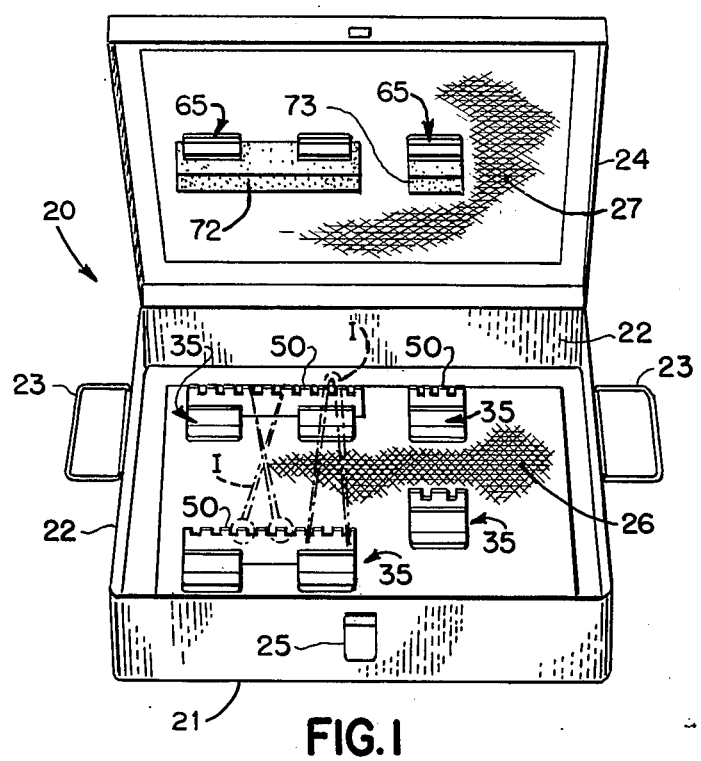
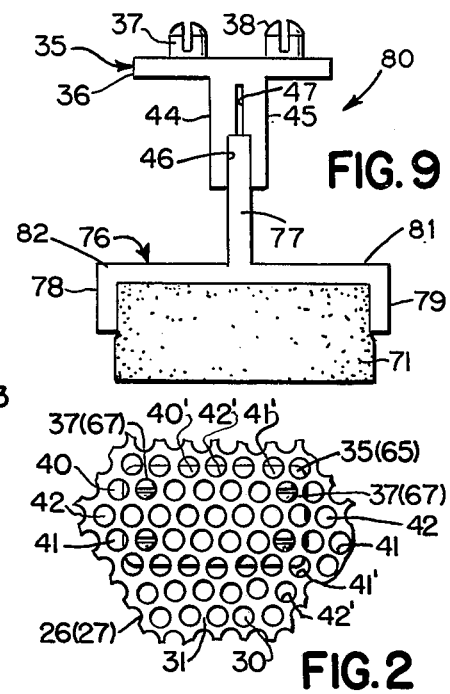
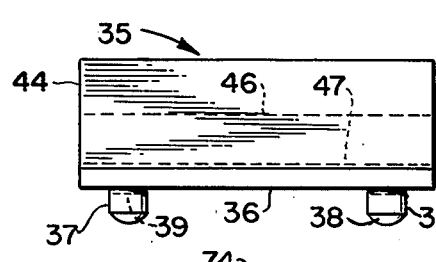
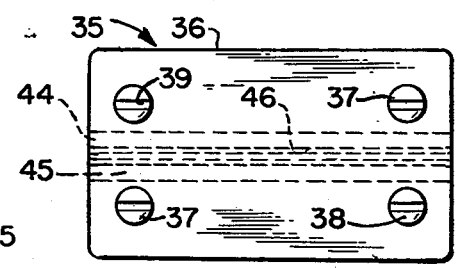
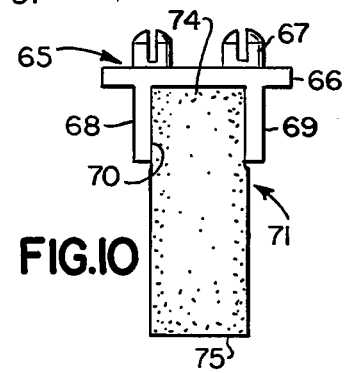
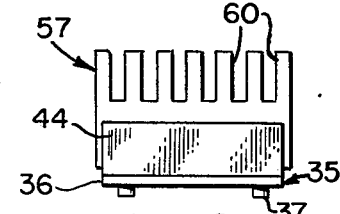
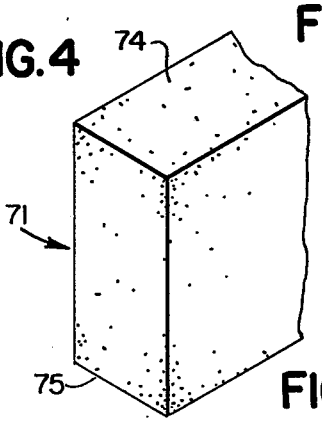
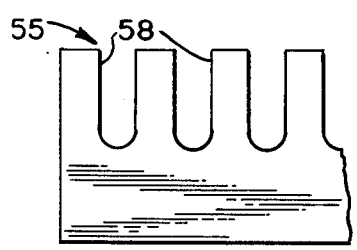
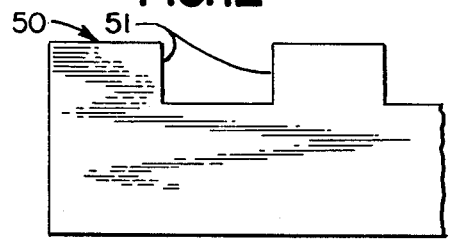
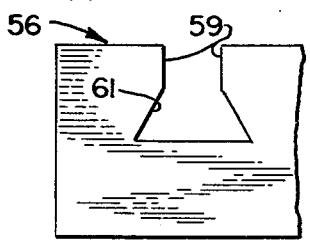

SUPPORTS FOR INSTRUMENT STERILIZATION

BACKGROUND OF THE INVENTION

1. Field of the Invention

This invention relates to article retaining devices and more particularly to modular supports for retaining instruments in selected positions in a sterilization tray.

2. Brief Description of the Prior Art

In preparation for sterilization, extremely delicate precision instruments, such as those used in eye surgery and the like, should not be placed loosely in a sterilization tray as their contact with the tray and with each other will dull cutting edges and disrupt coacting parts and other adjusted elements.

In the past, individual upstanding posts, bolted or otherwise affixed to apertures in the bottom of a sterilization tray have been arranged to hold the finger engaging rings of ring-handle instruments in a stacked assembly, thus preventing movement of the instruments about the tray during the sterilization process. However, since only ring-handle instruments may be so mounted, protection against movement is not provided for ringless instruments such as probes, forceps and the like. Furthermore, during the stacking of ring-handle instruments, contact between the cutting edges is often inadvertently made, resulting in undesirable dulling of the cutting edges, or damage to the instruments themselves.

Protection for medical instruments to be sterilized has also been provided by wrapping each instrument in steam permeable muslin or other materials, such as autoclavable paper, but such wrappings reduce the effectiveness of the autoclaving process, and cause excessive preparation time to be consumed.

It is therefore an object of the present invention to provide quick attaching modular supports for immovably positioning individual medical instruments in selected locations within a sterilization tray during the sterilization process, yet allowing maximum exposure of instrument surfaces to sterilizing steam.

SUMMARY OF THE INVENTION

According to the preferred embodiment of the invention, a plurality of modular supports are provided for mounting instruments at selected locations in a multi-apertured sterilization tray adjacent to, but out-of-contact with the sides of the tray. Each modular support has a base plate with outwardly projecting longitudinally split buttons adapted to be deformably inserted in mating apertures in the tray top or bottom. Each support baseplate has an upstanding member disposed on a side opposite the split buttons, with the member being slotted to receive and tightly hold a selected strip member having notches on an outer edge. Usually, at least two modular supports for each instrument are positioned on the bottom of a tray to cradle effectively therebetween in notches of associated members, an instrument to be sterilized.

To hold instruments in position in their associated notches, the deformable buttons of other baseplates, provided with means mounting blocks of resilient material, are inserted into related mating apertures in the top cover of the sterilization tray, disposed generally opposite instruments to be held in a desired position. Closure of the sterilization tray cover causes the block of resilient material to apply a gentle holding pressure against the cradled instruments.

The invention is pointed out with particularity in the appended claims. The present invention is best understood by reference to the following detailed description thereof when taken in conjunction with the accompanying drawings in which:

BRIEF DESCRIPTION OF THE DRAWING

FIG. 1 is a perspective view of a sterilization tray with modular instrument supports and hold-downs fixed therein;

FIG. 2 is a bottom view of a fragment of the perforated bottom side or a top view of the perforated cover of the sterilization tray of FIG. 1 with an instrument support base or a hold-down base fixed thereto;

FIG. 3 is a side view of an instrument support base;

FIG. 4 is an end view of the instrument support base of FIG. 3 with a strip held thereby;

FIG. 5 is a bottom view of the instrument support base;

FIGS. 6, 7, and 8 are side views of broken away ends of strips notched to hold and cradle instruments;

FIG. 9 is an end view of a bracket held by an instrument support base with the bracket securing a block of resilient material as a hold-down;

FIG. 10 is an end view of a hold-down base securing a block of resilient material;

FIG. 11 is an isometric view of the broken away end of a block of resilient hold-down material; and FIG. 12 is a side view, on a reduced scale, of an instrument support base with a length of notched strip held thereby.

DESCRIPTION OF THE PREFERRED EMBODIMENTS

As shown in FIG. 1, a sterilization tray 20 has a bottom side 21 with edges 22 and handles 23. A top side forming a cover 24 is hinged to the edges 22 to be held closed by the catch 25. Tray bottom 21 has a perforated panel 26 and cover 24 has a perforated panel 27 to freely admit and circulate steam for sterilization in tray 20. As shown in FIG. 2, panels 26 and 27 best contain a hexagonal array of perforations 30 as a hexagonal array provides more open area for a given size of web 31 between perforations 30 then would a rectangular array (not shown).

Referring now to FIGS. 2–5, an integrally molded instrument support base generally indicated as 35 has a baseplate member 36 which may have a rectangular configuration from which four buttons 37 extend. The buttons 37 taper slightly and terminate in a rounded end 38. The buttons 37 contain slots or splits 39 to allow them to resiliently deform and be forced into perforations 30 to be held securely. Buttons 37 are located on member 36 to engage four perforations 30 spaced the same distance apart along two rows 40 and 41 with an intermediate row 42 therebetween.

If desired, instrument support base 35 could have had its buttons 37 inserted in apertures 30 in the rows 40' and 41' with the row 42' therebetween. This would orient base 35 at 60 degrees to its indicated position in a clockwise direction. It may also be mounted in a position that is 60 degrees counterclockwise from its indicated position.

Instrument support bases 35 are molded from a plastic material of slight resilience and have body portions formed with outwardly extending members 44 and 45 which define a slot 46 for receiving a strip 50. A lower, narrower slot portion 47 below slot 46 allows members 44 and 45 to flex and tightly hold strip 50 with a force fit.

As shown in FIG. 7, strip member 50 contains notches 51 to receive and cradle articles to be sterilized, for example, surgical instruments I (FIG. 1) extending between two strips 50 spaced apart from each other. Different instruments require different notch configurations to hold them securely. As shown in FIGS. 6, 8, and 12, the strips 55, 56, and 57 contain notches 58, 59, and 60, respectively, of different widths and shapes. The notch 59 of strip 56 is wider at its inner portion 61 than at its mouth opening to hold a portion of an instrument forced into it. The strips 50 and 55–57 are molded or fabricated from plastic that can be cut to required lengths to hold specific instruments in a sterilization tray.

As shown in FIG. 10, a hold-down base 65 has a baseplate member 66 with four buttons 67 projecting from it which are identical to those of support base 35. Hold-down base 65 has two spaced apart outwardly extending members 68 and 69 with a comparatively wide channel 70 between them to receive and hold under compression the edge 74 and sides of a rectangular block 71 formed from a resilient heat resistant material such as silicone or other rubber-like compound than can be solid or foamed. As shown in FIG. 1, block 71 is cut to lengths 72 and 73. Length 72 spans two hold-down bases 65 and length 73 spans a single hold-down base 65. The width of block 71 is determined by the depth of the sterilization tray 20 so that its lower free edge 75 deforms to press gently on instruments cradled in the notches 51 of strips 50.

An alternate hold-down 80 is shown in FIG. 9. An instrument support base 35 fixed to cover panel 27 holds a bracket 76 by an outwardly projecting fin member 77 pressed in slot 46. Bracket 76 has a pair of laterally extending arm members 81, 82 with two downward extending, depending fingers 78 and 79 which hold under compression a horizontally disposed resilient block 71 forced therebetween.

Strips 50, 55, 56, and 57 may be glued, welded, or otherwise fixed in the slots 46 of the instrument support bases 35, or they may be secured by a force fit. This invention allows a supply of instrument support bases 35, hold-down bases 65, strips 50 and 55–57, and blocks 71 to be supplied for use with a sterilization tray 20 as modules to be assembled as required for specific instruments.

Prior to sterilization, the instrument support bases 35 and the hold-down bases 65 may be first fixed in a sterilization tray 20 after which strips 50 and blocks 71 are cut to required lengths and forced in place in their respective holders. Hold-down bases 65 are next selectively positioned on sterilization tray top 24 such that associated blocks 71 deform when top cover 24 is closed, to apply a firm holding pressure against the delicate instruments cradled in bases 65. The closed tray with enclosed instruments held securely against movement, is then ready for the sterilization process. The circulation of steam is substantially unimpeded for effective sterilization. To accommodate instruments slightly longer than the width of the tray 20 or for other purposes of arrangement, the instrument support bases 35 and the hold-down bases 65 may be rotated and fixed at 60 degrees to the positions shown in FIG. 1.

While this invention has been shown and described in the best forms known, it will nevertheless be understood that this is purely exemplary and that modifications may be made without departing from the spirit of the invention.

I claim:

1. A support base for articles to be sterilized in a sterilization tray of the type having a supporting panel having a uniform pattern of apertures disposed in rows forming an array comprising, in combination, a baseplate member for said support base, said baseplate member having multiple resilient deformable protrusions projecting from one side of said baseplate member and mutually spaced to engage some of the apertures in a supporting panel of a tray to removably mount said article support base in a plurality of differently oriented positions on a supporting panel, each protrusion having a generally cylindrical configuration to allow repeatable insertions in selected apertures, said baseplate member having on its other side a body portion extending outwardly in a direction opposite to said protrusions, said body portion including mutually spaced apart outwardly extending members defining a slot therebetween, and article supporting plastic strip means having one edge inserted and frictionally retained in said slot and having an opposite edge extending away from said protrusions and notched for cradling a portion of an article to be sterilized, whereby said strip means can be cut to such length as required by the position of the support base.

2. The invention defined in claim 1, wherein said deformable protrusions include a plurality of cylindrical buttons projecting from said baseplate member, the ends of said buttons each being slotted, said buttons deforming upon insertion into apertures, to compress said slotted ends.

3. The invention defined in claim 1, wherein said outwardly extending body members form a narrower slot below said slot receiving said strip means, said strip means being fixed in said slot by a force fit.

4. The invention defined in claim 1, wherein said resilient deformable protrusions comprise a plurality of spaced apart buttons arranged in rows for engaging spaced apart apertures in corresponding rows in a tray panel.

5. A hold down base for articles to be sterilized in a sterilization tray of the type having top and bottom sides movable from an open to a closed position, said sides having a plurality of apertures therein comprising, in combination, a baseplate member for said hold down base, said baseplate member having at least two resilient deformable protrusions projecting from said member for tightly engaging spaced apart apertures in a side of a tray to removably mount said hold down base thereon, each protrusion having a generally cylindrical configuration to allow repeatable insertion in a selected aperture, a block of resilient material, said baseplate member having a body portion extending outwardly in a direction opposite to said protrusions, said body portion including compression means for holding said block of resilient material under compression to removably mount said block in a position selected to allow said block to apply holding contact pressure against at least one article selectively disposed in a tray, said body portion having a slot therein and said compressing means including a fin member forceably inserted in said slot, said fin member having a pair of laterally extending arms, each of said arms having downwardly depending fingers, said block of resilient material being held under compression between said depending fingers.

* * * * *